United States Patent [19]
Strähle et al.

[11] Patent Number: 5,612,816
[45] Date of Patent: Mar. 18, 1997

[54] ENDOSCOPIC ATTACHMENT FOR A STEREOSCOPIC VIEWING SYSTEM

[75] Inventors: Fritz Strähle, Heubach-Lautern; Ulrich Sander, Oberkochen; Uwe Vry, Aalen, all of Germany

[73] Assignee: Carl-Zeiss-Stiftung, Heidenheim, Germany

[21] Appl. No.: 510,697

[22] Filed: Aug. 3, 1995

Related U.S. Application Data

[63] Continuation of Ser. No. 100,276, Aug. 2, 1993, abandoned, and a continuation-in-part of Ser. No. 875,634, Apr. 28, 1992, Pat. No. 5,321,447.

[30] Foreign Application Priority Data

Aug. 1, 1992 [DE] Germany .......................... 42 25 507.4
Jan. 21, 1993 [DE] Germany .......................... 43 01 466.6

[51] Int. Cl.$^6$ .......................... G02B 21/22; G02B 23/00; G02B 15/14
[52] U.S. Cl. .......................... 359/376; 359/377; 359/432; 359/683; 351/216
[58] Field of Search .......................... 359/423, 432, 359/434, 362, 363, 376, 378, 377, 435, 715, 716, 683; 351/216, 205

[56] References Cited

U.S. PATENT DOCUMENTS

| | | | |
|---|---|---|---|
| 3,486,806 | 12/1969 | Werner | 359/404 |
| 4,061,135 | 12/1977 | Widran et al. | 600/111 |
| 4,149,769 | 4/1979 | Zobel | 359/432 |
| 4,364,629 | 12/1982 | Lang et al. | 359/377 |
| 4,601,550 | 7/1986 | Yoshino et al. | 359/377 |
| 4,862,873 | 9/1989 | Yajima et al. | 128/6 |
| 4,964,710 | 10/1990 | Leiner | 359/434 |
| 4,989,023 | 1/1991 | Sakurai et al. | 354/62 |
| 5,009,487 | 4/1991 | Reiner | 359/376 |
| 5,122,650 | 6/1992 | McKinley | 250/208.1 |
| 5,282,085 | 1/1994 | Volkert et al. | 359/434 |
| 5,321,447 | 6/1994 | Sander et al. | 359/376 |

FOREIGN PATENT DOCUMENTS

| | | | |
|---|---|---|---|
| 19792 | 12/1980 | European Pat. Off. . | |
| 1996605 | 11/1968 | Germany . | |
| 1766803 | 9/1971 | Germany . | |
| 3723574 | 1/1988 | Germany | 359/377 |
| 4116810 | 11/1992 | Germany . | |
| 02654485 | 3/1970 | U.S.S.R. | 359/377 |
| 1061052 | 3/1967 | United Kingdom | 359/377 |

*Primary Examiner*—P. M. Dzierzynski
*Assistant Examiner*—Mohammad Y. Sikder
*Attorney, Agent, or Firm*—Walter Ottesen

[57] ABSTRACT

The invention is directed to a stereoscopic endoscope wherein an intermediate image is generated in a rod-shaped endoscope attachment. The intermediate image is imaged into the focal plane of an objective. The objective can be the main objective of a surgical microscope with the objective having a long focal length or the main objective of a stereoscopic recording system. The main objective and an in-coupling optic conjointly define an inverted telescope.

31 Claims, 8 Drawing Sheets

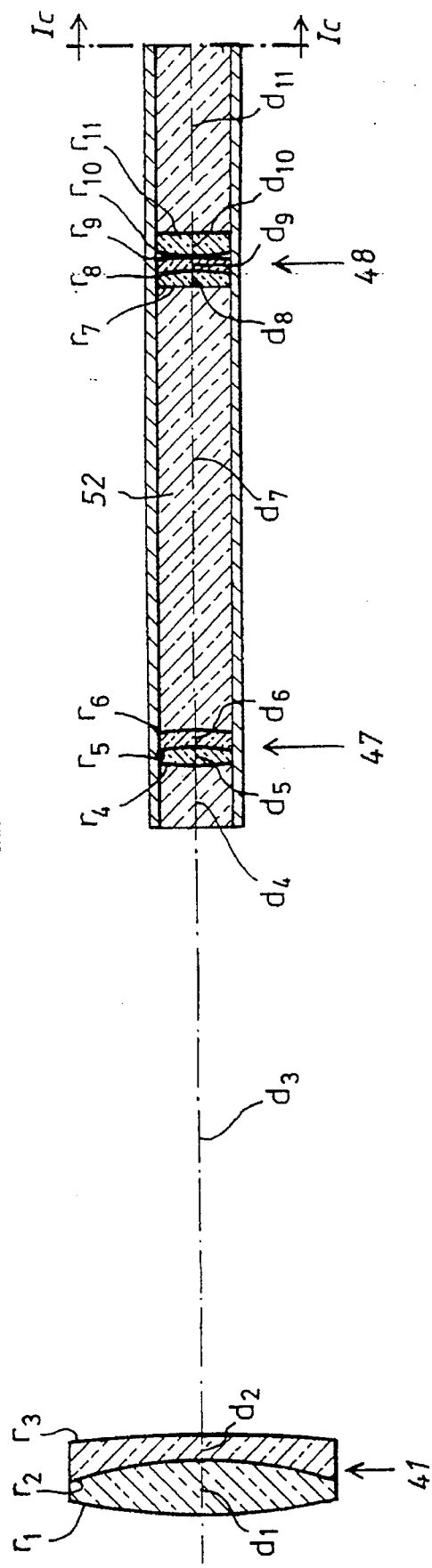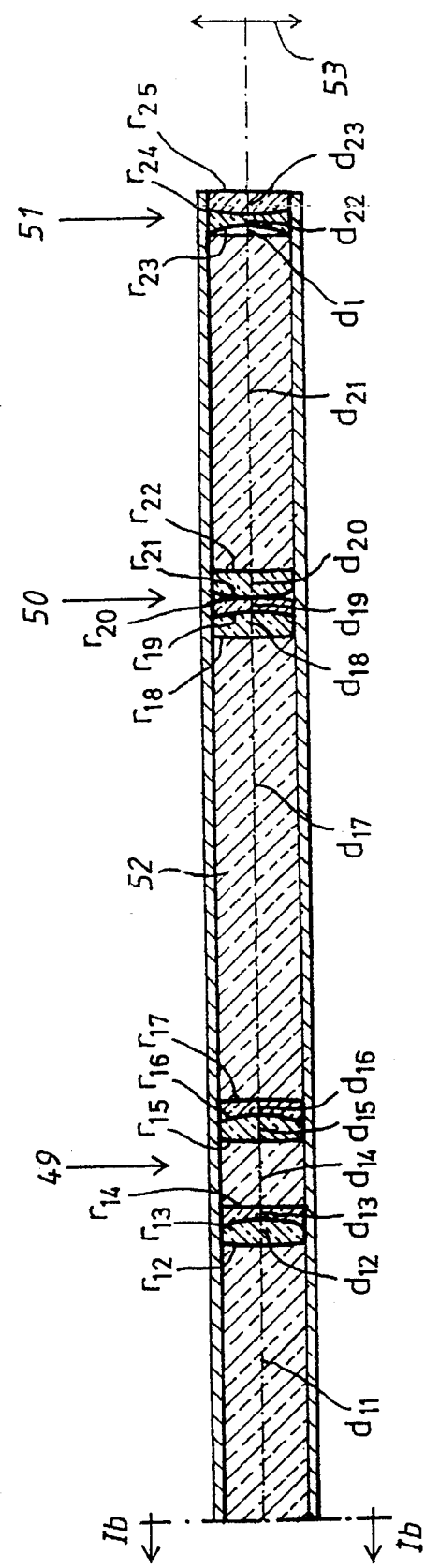

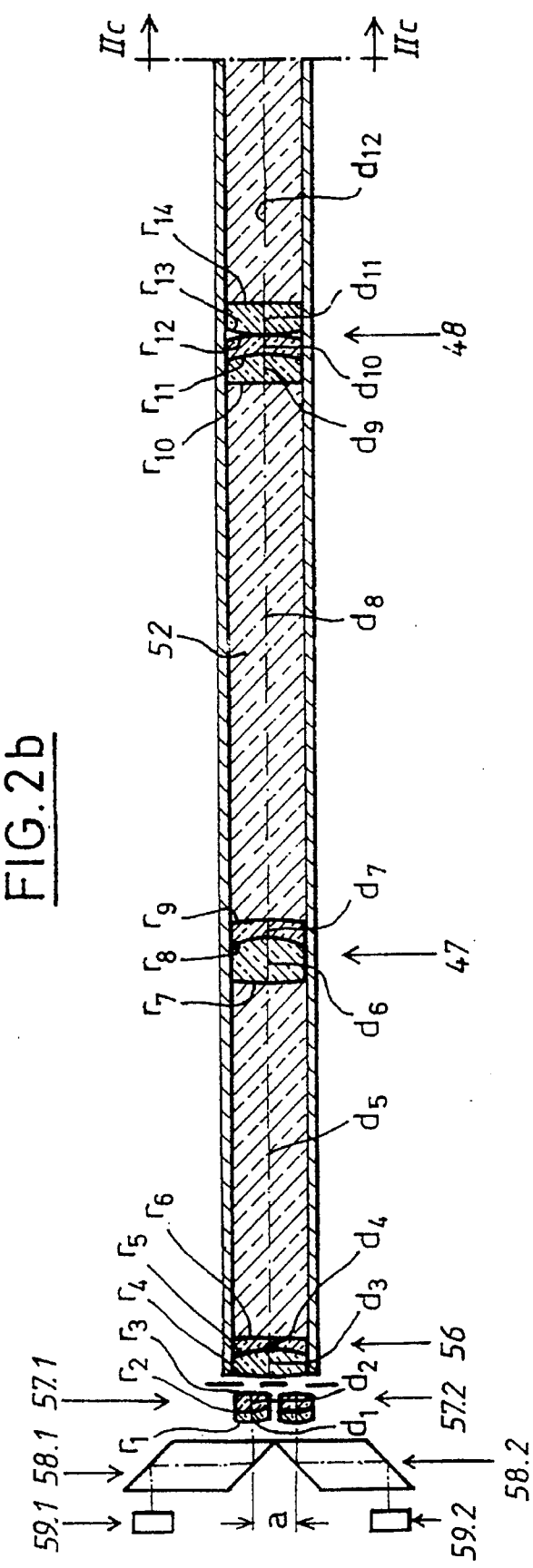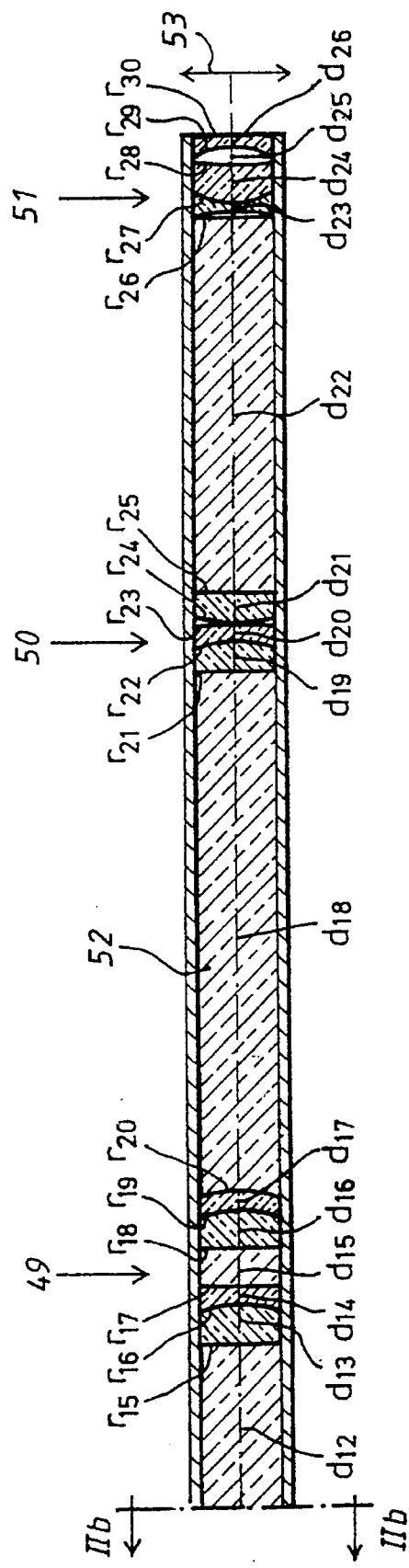
FIG. 2b
FIG. 2c

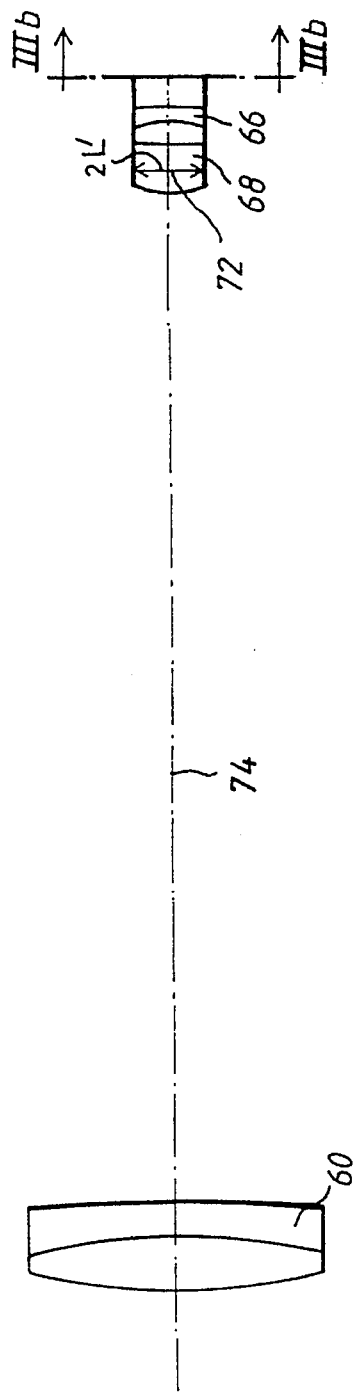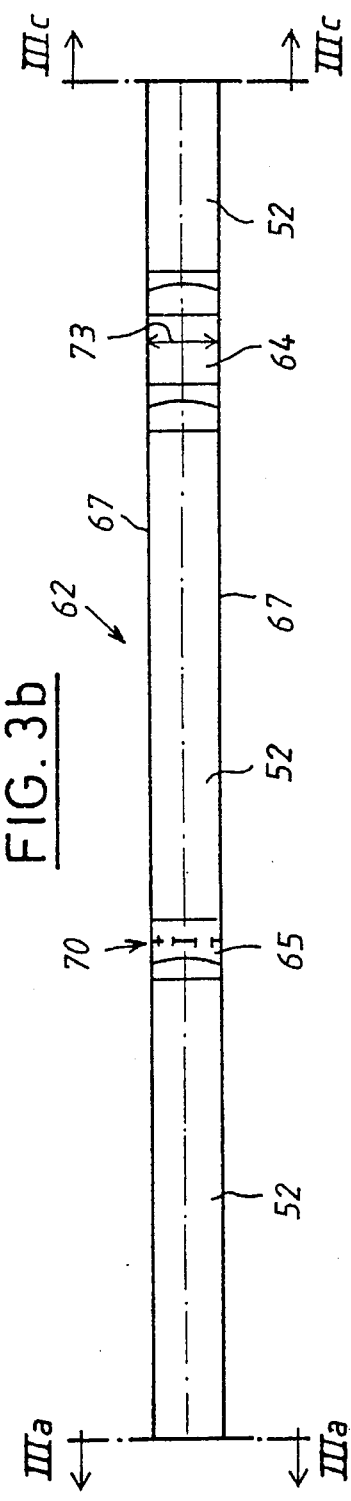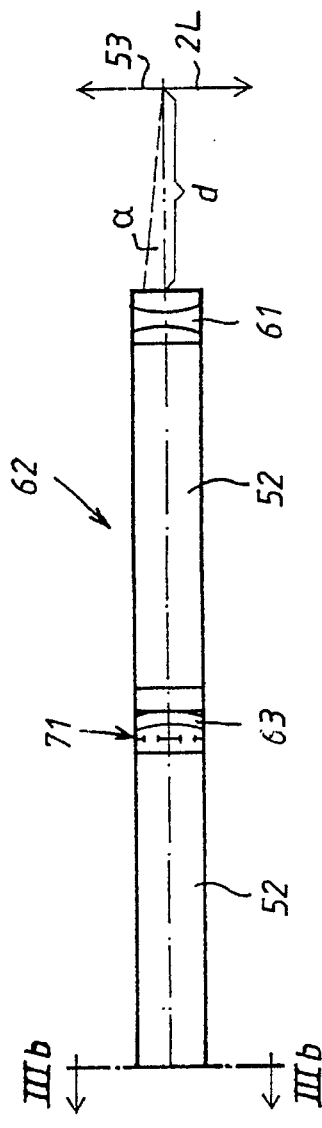

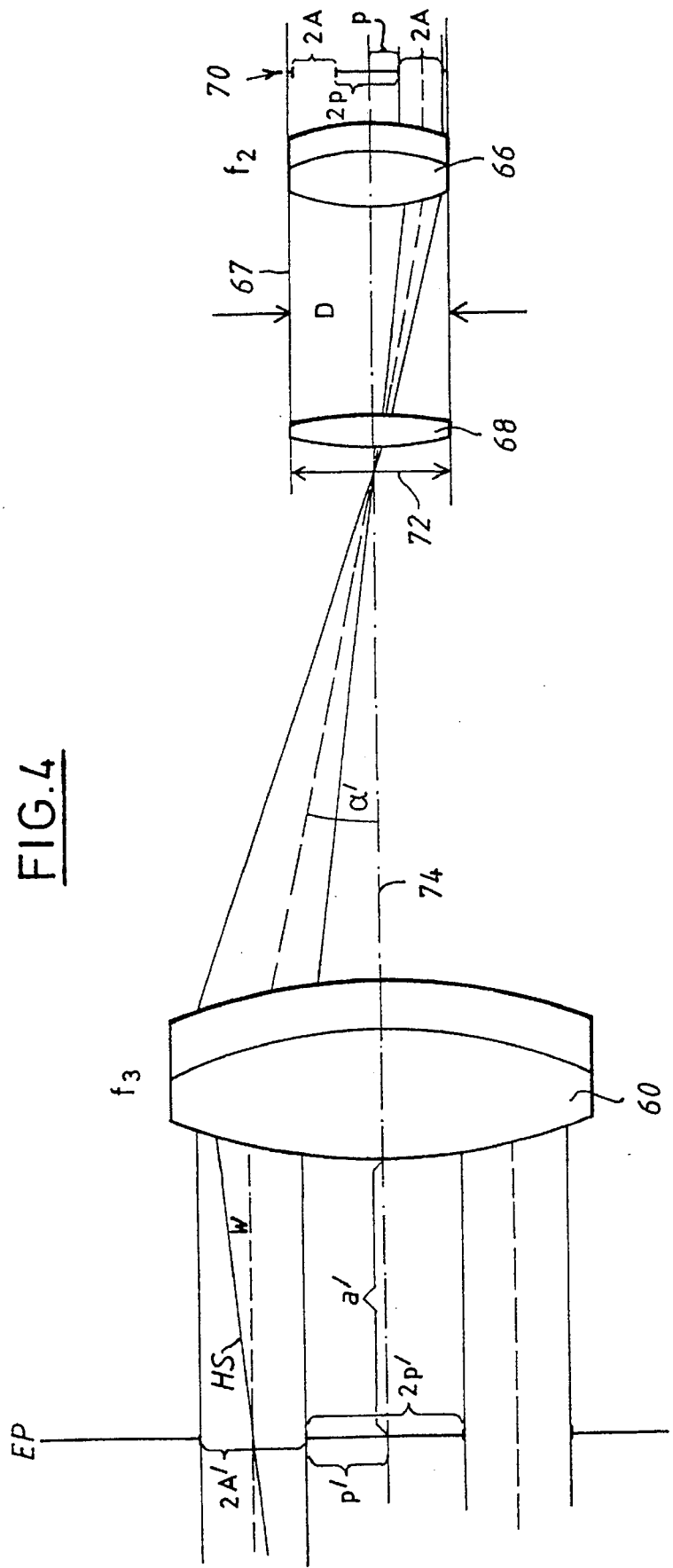

ENDOSCOPIC ATTACHMENT FOR A STEREOSCOPIC VIEWING SYSTEM

This is a continuation-in-part application of U.S. patent application Ser. No. 07/875,634, filed Apr. 28, 1992, (now U.S. Pat. No. 5,321,447) and claiming priority of German patent application P 41 14 646, filed May 4, 1991 as well as of U.S. patent application Ser. No. 08/100,276, filed Aug. 2, 1993, and claiming priority of German patent applications P 42 25 507.4 and P 43 01 466.6, filed Aug. 1, 1992 and Jan. 21, 1993, respectively.

BACKGROUND OF THE INVENTION

It is known to use flexible or rigid endoscopes for surgery in narrow and deep cavities of the body. In most cases, the viewing channels are defined by image conductors. The transmission of images via image conductors has, however, serious disadvantages with respect to color quality and the resolution obtained. These disadvantages are avoided in rigid endoscopes.

Precise surgical work often requires a spatial image impression. Rigid endoscope configurations are known having different structural lengths and diameters as are stereoscopic systems. In this connection, reference may be made to published German patent application 1,766,803, German utility model registration 1,996,605 and U.S. Pat. No. 4,061,135. These known systems have an elongated base body in which two parallel sets of optics are arranged for stereoscopic viewing or photography. The use of separate optics for the stereo component beam paths leads, however, in several embodiments together with the instrument and viewing channel to a total tube diameter in the range of 25 to 30 mm which greatly limits the area of application of such endoscopes.

The two viewing channels must be adjusted with respect to each other in a complex manner for good stereoscopic imaging; more specifically:

a) with respect to the image position, with the position of the two images being different because of the given refractive index tolerance, thickness tolerance and radii tolerance and only being permitted to vary within narrow limits; and, b) with respect to the binocular error, with the optical axes of both viewing channels being strictly aligned parallel to each other with a deviation of a few angular minutes.

The required adjustment in such systems would have to be made ideally within the endoscope tube which however can hardly be done because the endoscope tube is not easily accessible for manipulation.

For a rigid endoscope, U.S. Pat. No. 4,364,629 discloses utilizing a rod-shaped accessory objective in a surgical microscope in lieu of the main objective having a long focal length. In this known solution, the large stereo basis of the surgical microscope is adapted to the stereo basis of the accessory objective with a prism system. The stereo basis of the accessory objective is less by approximately a factor of ten. A disadvantage of this known solution is that the stereo angle and therefore also the stereo impression is reduced by the same factor of ten. For practical applications, such as for laparoscopy, the largest possible objective field diameters are required which perforce reduces the stereo angle still further as will be made clear in the disclosure which follows. For this reason, the actual task of stereoscopic imaging cannot be satisfactorily solved with this known suggestion.

A further disadvantage of the known solution is that the large diameters of the two stereo beam paths of the surgical microscope (apparatus pupils) of approximately 16 mm are adapted with the prism system alone to the stereo beam paths of the accessory objective with the stereo beam paths, in turn, being less in diameter by approximately the factor 10. This causes unacceptably intense vignetting to occur with all generally known disadvantages for tile imaging characteristics. An amplification of the vignetting effect occurs also because the apparatus pupils of the surgical microscope are not identical to the exit pupils of the attachment objective.

U.S. Pat. No. 5,122,650 discloses a solution for an optical system for displaying three-dimensional endoscopic images. This solution provides that the object is imaged with a main objective at infinity and that for the two stereoscopic imaging beam paths respective imaging optics are provided rearward of the main objective for generating two mutually adjacent stereo component images as intermediate images in the finite range. These intermediate images are either imaged on two CCD chips or are transmitted via video electronics onto a monitor and are viewed with special spectacles or the intermediate images are transmitted via a rod-shaped optic into a viewing plane for viewing. A disadvantage of this solution is that a large diameter for the optical system is required because of the imaging of two mutually-adjacent stereo component images in one plane. A diameter of the optical system of at least $2b$ is necessary if it is intended to transmit an intermediate image of an object with the intermediate image having the magnitude b.

Published German patent application 4,116,810 discloses the use of a surgical microscope equipped with an endoscope. An endoscope is placed upstream of the surgical microscope such that a scissors-like joint piece is arranged between the main objective of the surgical microscope and the ocular of an endoscope. The joints are intended to be self-restraining so that they remain stationary in each image position in which they are placed by the physician. In this arrangement, neither data is given as to whether the endoscope even supplies a three-dimensional image having a satisfactory stereo basis nor how a stereoscopic image transmission from the endoscope to the surgical microscope should take place. Accordingly, doubt is present as to whether the surgeon receives a usable three-dimensional image by means of this arrangement.

SUMMARY OF THE INVENTION

It is an object of the invention to keep the tube diameter of a stereoscopic endoscope as small as possible and to nonetheless guarantee a good stereo impression having excellent imaging qualities, resolution and depth of field. It is a further object of the invention wherein the following are pregiven by means of the tube diameter used: the optical requirements with respect to image size, pupil diameter and the stereo basis.

The system according to the invention includes a rod-shaped attachment which cooperates with the stereoscopic viewing system. The endoscopic attachment includes an optical system having a clear diameter D with the imaging system being common for both stereoscopic beam paths. The imaging optic generates an intermediate image of the object to be viewed. Furthermore, an additional imaging system is provided by means of which the apparatus pupils and the stereo basis of the viewing system are demagnified and imaged in the attachment so that the sum of the image of the apparatus pupils of the viewing system and of the image of the stereo basis of the viewing system corresponds to the clear diameter D of the imaging optics within the attachment. At the same time, the additional imaging system images the intermediate image at infinity. Two stereo component images of the intermediate image occur in the viewing system as in a stereo microscope.

In the stereoscopic endoscope of the invention, the object-end stereo angle is proportional to the viewing-end stereo angle and inversely proportional to the imaging scale when the object is imaged in the intermediate image at an imaging scale ($\beta$). The stereo angle at which the intermediate image is generated is maintained when coupling into the viewing system.

It is advantageous when the object is intermediately imaged further within the attachment and forward of the intermediate image plane. The endoscope attachment together with a surgical microscope in the form of a stereoscopic viewing system then permits the stereoscopic object to be viewed upright and unreversed. For this purpose, the imaging system can comprise an endoscope objective and a transmission system. The transmission system images the intermediate image generated by the endoscope objective in the intermediate image plane and, at the same time, images the entrance pupil of the endoscope objective in the image of the apparatus pupil. Additional intermediate images can be provided for longer endoscope attachments.

The additional imaging system together with a portion of the imaging optics in the endoscope attachment conjointly define a reversed quasi Kepler-like telescope. The diameter of the apparatus pupil is demagnified in the same ratio as the stereo basis by means of this inverted telescope. In this way, the required conditions with respect to the size of the image as well as with respect to the size of the pupils are satisfied. The entire intertwined beam path can in this way be transmitted through the narrow tube of the attachment without vignetting of the image and pupil. Even several beam paths such as two beams paths for a primary viewer and two beam paths for an assistant viewer and further documentation beam paths can be transmitted in a single tube via a single optic. The intertwining of the beam paths does not constitute a disturbance. Such a transmission of several viewing channels was not previously possible with the state of the art.

The advantages obtained with the invention include especially that an optical system common to both stereoscopic beam paths is used for imaging the object and for transmitting the intermediate image. Another advantage is that the diameter of the optical elements is smaller compared to the state of the art and a still further advantage provides that the parameters specific to the endoscope such as tube diameter, tube length, stereo angle, depth of field, object field diameter, resolution capability and working distance are mathematically adapted to the particular requirements for different applications.

A still further advantage is seen in that an adjustment of image position and binocular error of two stereo component images is no longer present as required for the known systems having separate optics for the stereo channels. A significant advantage is furthermore that the stereo basis of the apparatus pupils can be reduced proportionally to the focal length of the viewing-end objective of the inverted telescope without thereby deteriorating the stereo impression.

In the optical system of the invention, the obtainable reduction of the diameter of the optical elements and therefore of the endoscope tube, is significant. The optical system disclosed in U.S. Pat. No. 5,122,650 requires a diameter of the optical elements of 6 mm for the transmission of an intermediate image having a size of 3 mm. In contrast, with the optical system according to the invention, only a diameter of 3 mm is required for the transmission of an intermediate image of the same size. This means, for a same size diameter of the optical elements, the image information transmitted by the optical system according to the invention is four times greater than for the image transmission provided by the optical system disclosed in U.S. Pat. No. 5,122,650.

According to an advantageous embodiment of the invention, the intermediate image generated within the attachment is imaged into the stereoscopic component images at infinity by means of a main objective which is a component of the additional imaging system. This stereoscopic imaging takes place with viewing via the two viewing channels of the tube having oculars. A magnification system (Galilei telescope for changing the magnification or pancratic telescope) or an optical divider for connecting additional viewing and documentation means (miniature camera, TV, 3DTV) can be placed between tube and objective.

This stereoscopic imaging can however also take place via two spatially separated but identically assembled imaging channels of a stereoscopic TV recording system.

The ratio of the spacing 2(A'+p') of the two stereoscopic imaging channels (stereo basis) to the focal length (f) of the objective determines the stereo angle important for the stereo impression. The same stereo angle and therewith also the same stereo impression is obtained at a reduced focal length (f) with a correspondingly reduced stereo basis. In this way, dimensions of the objective are obtained for stereo-TV endoscopes which permit integration of the objective into the rod-shaped optical system with the advantages of compactness and lengthening of the tube resulting therefrom.

The solution provided by the invention also makes possible an optimal optical correction of the overall imaging system. The system according to the invention is comparable to the imaging characteristics of a conventional surgical microscope with reference to the optical imaging characteristics (resolution, color fidelity, depth of field, stereo impression).

BRIEF DESCRIPTION OF THE DRAWINGS

The invention will now be described with reference to the drawings wherein:

FIGS. 1b and 1c show a section view of the rod-shaped attachment of the arrangement shown in FIG. 1a;

FIGS. 2b and 2c show a lens section of the rod-shaped attachment of FIG. 2a;

FIGS. 3a, 3b and 3c together show the endoscopic attachment;

FIG. 4 is an enlarged schematic of the stereoscopic beam paths in the region of the inverted telescope;

DESCRIPTION OF THE PREFERRED
EMBODIMENTS OF THE INVENTION

Figure 1A:
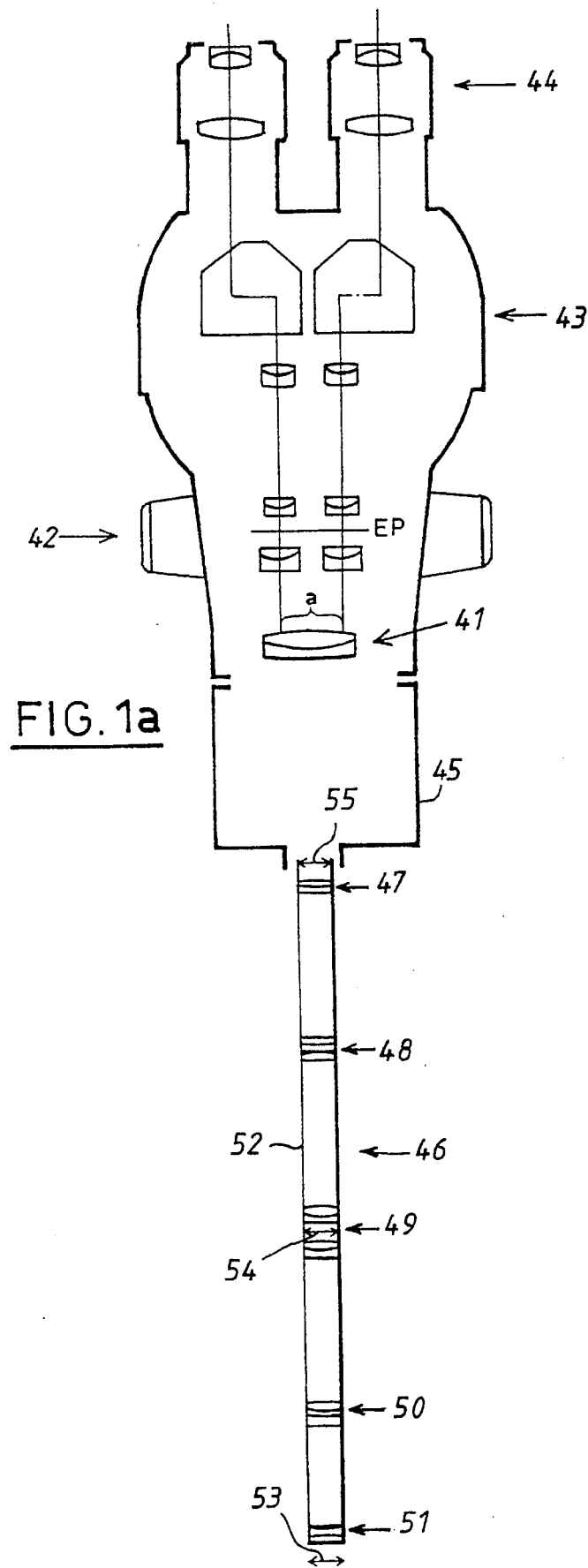
FIG. 1a is a section view of a first embodiment of the invention for stereoscopically viewing through a surgical microscope.

FIG. 1a shows the schematic configuration of a surgical microscope comprising a main objective 41, a magnification system 42, a barrel 43 and an ocular 44. A rod-shaped optical attachment 46 is connected via an attachment piece 45 to the surgical microscope. The attachment 46 comprises an object-end objective 51, a rear imaging lens system 50, a rear field lens system 49, a forward imaging optic 48 and a forward field lens system 47. Glass rods 52 are provided in lieu of air spaces between the lens systems to extend the structural length.

The viewed object 53 is imaged via a first intermediate image 54 and a second intermediate image 55 in the focal plane of the main objective 41. The first intermediate image 54 is formed in the rearward field lens system 49 and between the forward field lens system 47 and the main objective 41. The main objective 41 and the two tube lenses in tube 43 conjointly image the second intermediate image 55 as two stereo component images in the focal plane of the ocular 44. The main objective 41 and the forward imaging optic 48 and the field lens system 47 conjointly define an inverted telescope which ensures a vignetting-free in-coupling and an intertwining of the separate stereo beam paths in the endoscope attachment. The stereo component beam paths are spatially separate in the plane of the apparatus pupils (EP). The in-coupling into the surgical microscope takes place while maintaining the stereo angle at which the intermediate image 55 is generated in the endoscope attachment.

Figure 2A:
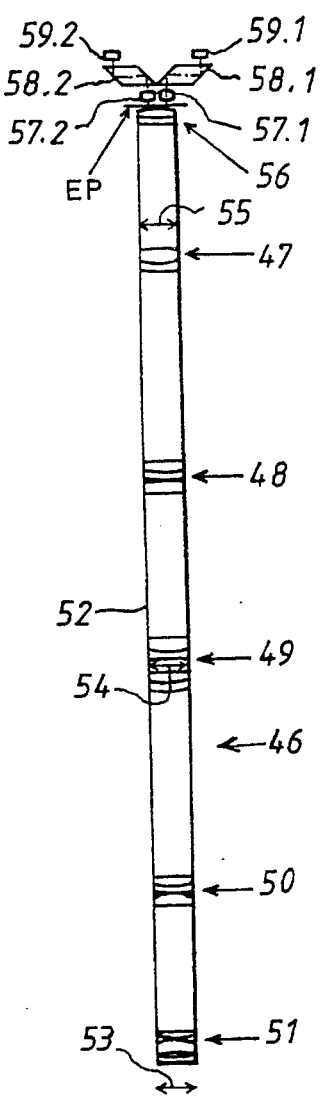
FIG 2a is a second embodiment of the invention for stereoscopically imaging while using a stereo-television camera having two CCD-image receivers.

In FIG. 2a, a main objective 56 is provided in addition to the elements (47 to 51) at the viewing end of the rod-shaped optical system. The elements (47 to 51) correspond to those in the embodiment of FIG. 1a. Two identical component objectives (57.1 and 57.2) for the two stereoscopic beam paths are arranged after the main objective 56. Path-folding prisms (58.1 and 58.2) to physically separate the stereo beam paths are arranged downstream of component objective (57.1 and 57.2) as well as CCD receivers (59.1 and 59.2) for stereoscopically recording the component images.

The objective 56 is adapted to the diameter of the tube so that an effective lengthening of the tube results. The focal length of the objective 56 is less than the focal length of the main objective 41 in FIG. 1a. For this reason, the stereo basis can be reduced proportionally to the focal length without the stereo impression deteriorating thereby.

The designation (EP) identifies the apparatus pupil or the entrance pupil of the particular optical system and (a) identifies the stereo basis.

Furthermore, additional beam paths for viewing by a second person or for documentation can be provided which are intertwined with the stereoscopic beam paths for the main observer. This can, for example, be provided simply with a configuration of the surgical microscope above the main objective 41 as disclosed in U.S. Pat. No. 4,991,947.

The optical assembly of the endoscope of FIG. 1a between the object and objective 51 and the main objective 41 is shown in FIG. 1b and 1c the endoscope of FIG. 2a is shown enlarged in FIG. 2b and 2c. The data for the radii (r), thicknesses and spacings (d) as well as the types of glass used for the optical components are presented in Table I (FIGS. 1b and 1c and Table II (FIGS. 2b and 2c). Reference character (r) identifies the particular surface radius of curvature. The thicknesses and spacings are measured along the optical axis (shown as a dot-dash line) between the mutually adjacent surfaces at the intersect points with the optical axis of each two mutually adjacent surfaces. Reference numeral 52 identifies the glass intermediate pieces for extending the structural length. The endoscope of FIGS. 1b and 1c Table I includes an air gap ($d_1$) of 2 mm between the objective 51 and the next-adjacent glass intermediate piece 52. A corresponding air gap ($d_1$) of 1.5 mm is provided in the endoscope of FIGS. 2b and 2c.

Two intermediate images (54, 55) are generated in the arrangements of the optical element shown in FIGS. (1b, 1c) and (2b, 2c). In lieu of these arrangements, another even-numbered quantity of intermediate images is possible so that an object can be correctly viewed with respect to upright correctness and lateral correctness as well as stereoscopic correctness. In principle, uneven numbers as to intermediate images are possible when, for example, by inverting the camera and when the view is inverted from left to right, the correct display is guaranteed with respect to elevation and side (unreversed) as well as stereoscopy. In this context, parts of the disclosed lens systems (47 to 51) can be advantageously applied many times. Variations of individual parameters of the sets of data provided in Tables I and II can likewise lead to a comparably good image result.

The attachment of the stereo endoscope shown in FIGS. 3a to 3c comprises a viewing-end objective 60 (main objective), an in-coupling optic (66, 68), a transmission optic 62 and an object-end objective 61 (endoscope objective). In the embodiment shown, the transmission optic 62 comprises three individual elements (63, 64, 65) and the glass rods 52. The transmitting optic 62 can however also comprise a multiple number of these elements. Here too, the main objective 60, in-coupling optic (66, 68) and the adjacent element 65 of the transmitting optic conjointly define an inverted Kepler telescope. A field lens 68 is provided in the vicinity of the intermediate image 72 within the telescope. With the field lens 68, the main beam path HS can be influenced and, for example, be made telecentric in the attachment 67 at the location of the intermediate image 72.

The intermediate image (72, 73) as well as the pupils (70, 71) are transmitted at a scale of 1:1 by means of the optical system for the stereoscopic transmission of the stereo beam paths (transmission optics) (63, 64, 65). This transmission can also take place with the aid of gradient rods. Gradient rods have a radial refractive index profile and imaging (self-focusing) characteristics. These gradient rods are commercially available under the trade name SELFOC. The gradient rods are preferably applied with small endoscope tube diameters of less than 3 mm.

The part of the attachment shown in FIG. 4 is in principle the same for all different applications. The intersect points are the apparatus pupils (EP) of the stereoscopic viewing system specific to the application. The diameter (2A'), the spacing from the main objective (a') and spatial separation 2(p'+A')=stereo basis of the apparatus pupils (EP) are different in accordance with application. The apparatus pupils (EP) are coincident with the images of tile entry pupil (71) of the endoscopic attachment (exit pupil).

The diameter of the apparatus pupil or exit pupil (EP) of the endoscope is identified with (2A') and the stereo basis corresponding thereto is identified by 2(p'+A'). The size of the pupil transmitted in the endoscope tube 67 is identified by (2A) and the stereo basis corresponding thereto is identified by 2(p+A). Reference character (D) is the clear diameter of the optic of the endoscope tube and reference numeral 72 identifies the intermediate image viewed from the main objective 60. The main beam (HS) of the imaging and the axis parallel to the optical axis 74 conjointly define the angle (w).

To adapt the lens system in the rod-shaped attachment having a clear diameter (D) to an optical system specific for a particular application the following conditions are satisfied:

$$2L' = 2f_3 \cdot \tan w = D$$

$$2(2A+p) = D$$

and $$\frac{p}{p'} = \frac{A}{A'} = \frac{f_2}{f_3}.$$

The following stereo angle results from the foregoing:

$$\tan\alpha' = \frac{p' + A'}{f_3}$$

The imaging scale for imaging the pupil is so selected that the image of the sum of the stereo basis (2(p'+A')) and the pupil diameter (2A') corresponds to the clear diameter (D) in the attachment.

Two or even several stereoscopic beam paths are transmitted with a single optical system arranged centrically to the optical axis 74 with the transmission system (63, 64, 65) shown in FIGS. 3a to 3c. These stereoscopic beam paths supply respective stereo images which are free of vignetting and which maintain the stereo impression while utilizing the entire clear optic diameter. This transmission takes place by means of a plurality of imagings in the scale of 1:1 of the intermediate image (72, 73) as well as of the pupils (70, 71). The number of these imagings determines image orientation and the stereoscopically correct or false depth perception.

The object field diameter 2L specific to the application and the working distance (d) can be determined with the endoscope objective 61. The following then applies for the imaging scale ($\beta$) of object to intermediate image:

$$\beta = L'/L.$$

The reference character (2L') identifies the field diameter in the intermediate image 72. The optical imaging characteristics such as resolution and depth of field are perforce tied to this imaging scale ($\beta$) in a manner known per se. The stereo angle ($\alpha$) and therefore the stereo impression is inversely proportional to the imaging scale ($\beta$):

$$\alpha = \alpha'/\beta$$

The stereo impression therefore remains unchanged for $\beta=1$. For $\beta>1$, a reduced stereo impression is obtained but an increasing depth of field is a desired side effect for endoscopic applications.

Figure 5:
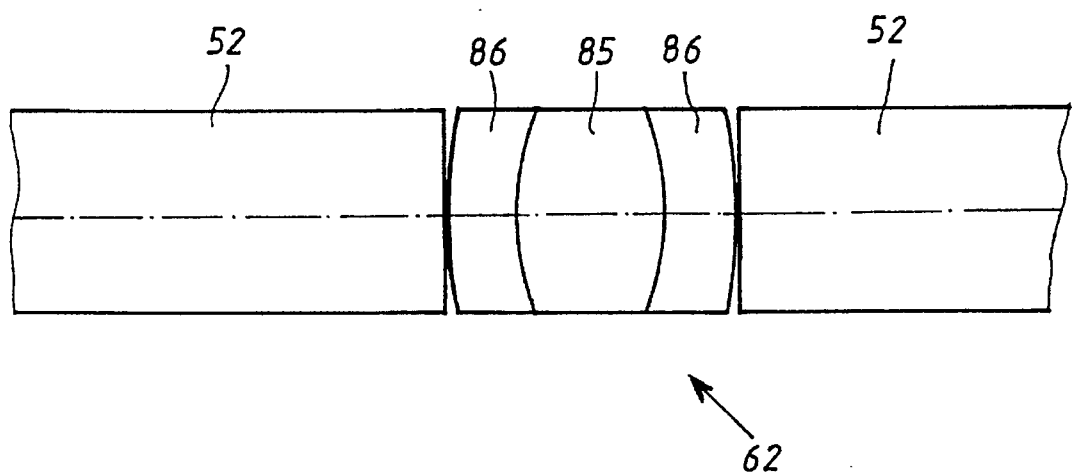
FIGS. 5 and 6 show embodiments of the transmission optics made of identical and symmetrical cemented components; and, FIGS. (7a, 7b) and (8a, 8b) are section views taken through the lens of two further embodiments of the invention.
Figure 6:
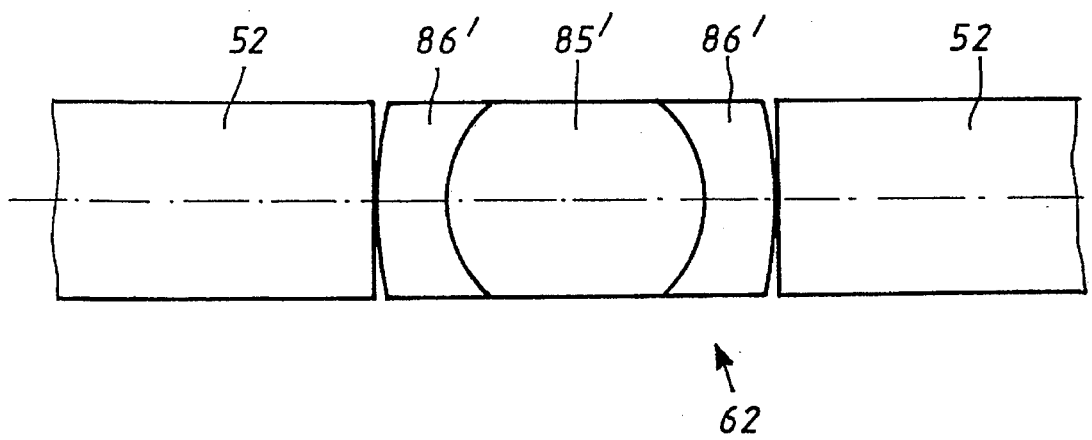

In the embodiments shown in FIGS. 5 and 6, the glass rods for the transmission optics 62 are again identified by reference numeral 52. The cemented elements comprise a biconvex lens (85, 85') which is arranged between two identical meniscus lenses (86, 86'). The axial length of the meniscus lenses (86, 86') is less than half their diameter. The glass rods 52 join directly (without an air gap) to the meniscus lenses. The biconvex lens 85' in FIG. 6 is a spherical lens.

Figure 7A:
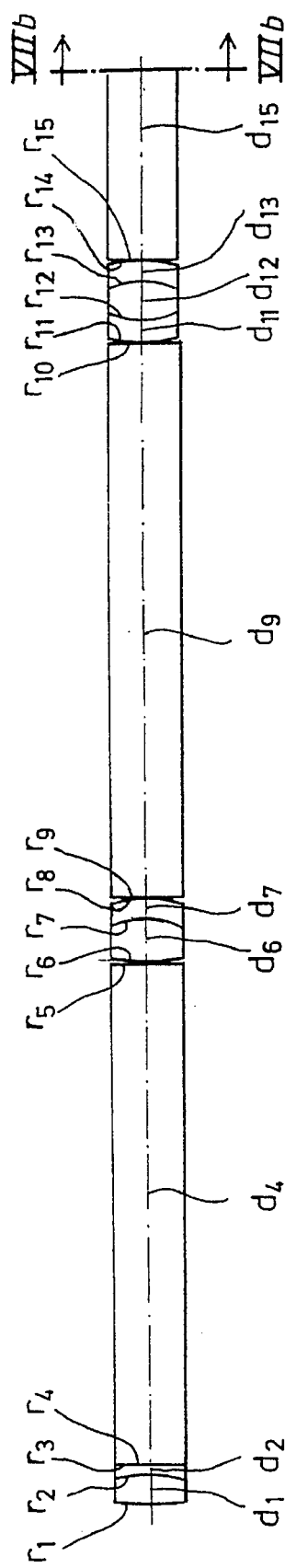
Figure 7B:
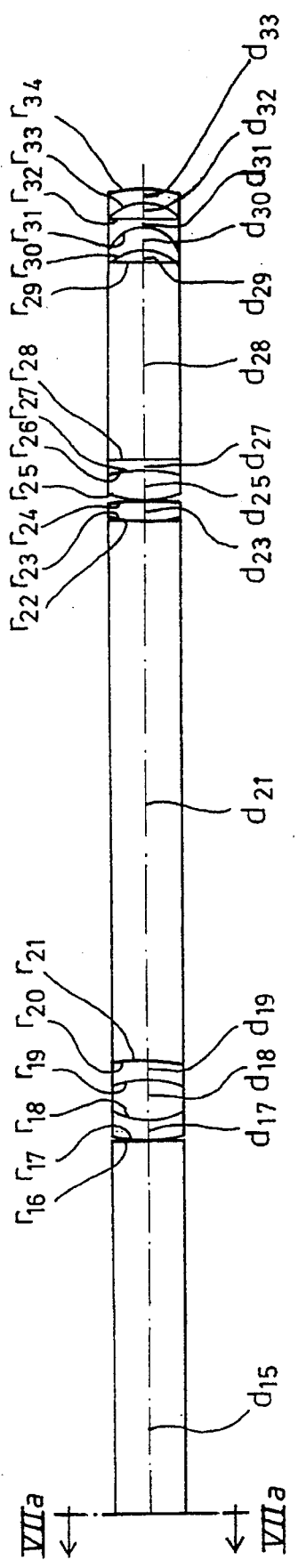
Figure 8A:
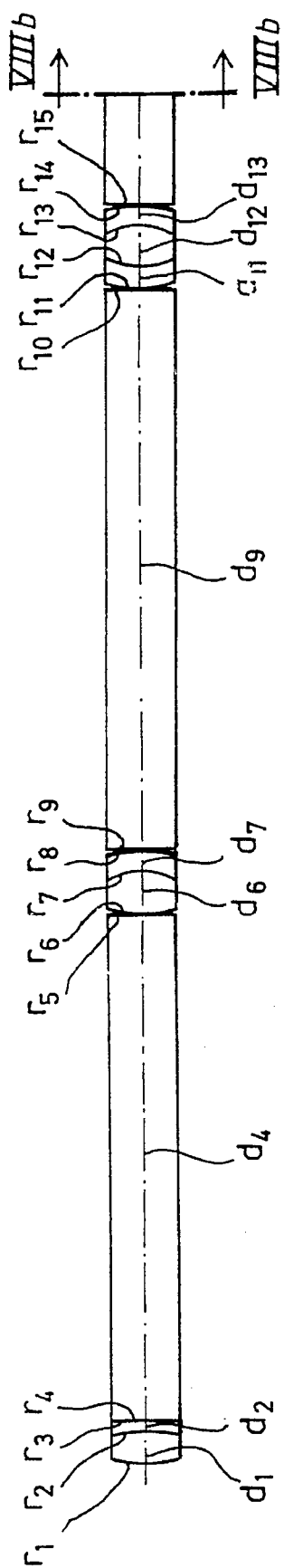
Figure 8B:
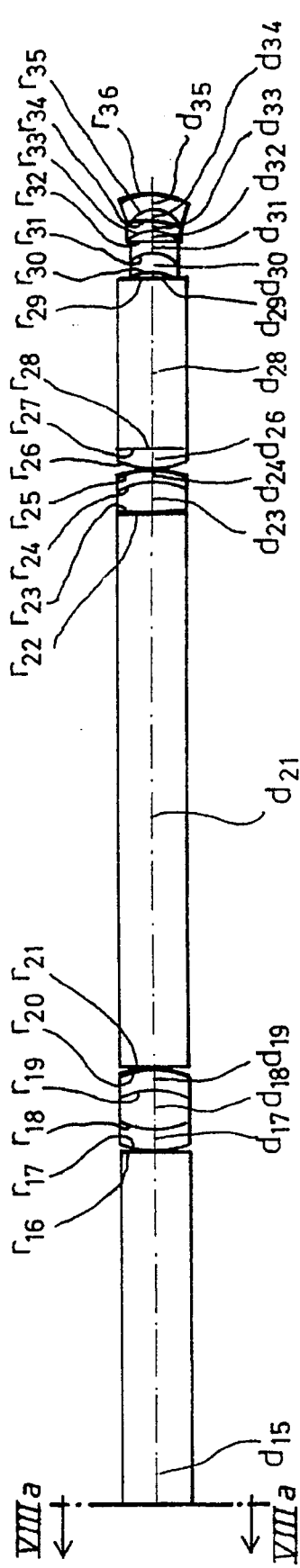

Two additional embodiments for rod-shaped endoscopic attachments are shown in FIGS. 7 and 8. The optical data for the surface curvature radius $r_i$, thicknesses and distances $d_i$ and the glasses used in the embodiment of FIGS. 7a and 7b are listed in Table III and for the embodiment of FIG. 8 in Table IV. The distances and thicknesses are measured along the optical axis 74 between the intersect points of the particular surfaces with the optical axis. The individual surfaces are numbered in Tables III and IV continuously starting with the main objective. The endoscope attachment in FIGS. 7a and 7b has an image angle of 45° and the attachment of FIGS. 8a and 8b has an image angle of 60°.

It is understood that the foregoing description is that of the preferred embodiments of the invention and that various changes and modifications may be made thereto without departing from the spirit and scope of the invention as defined in the appended claims.

TABLE I

| Optical Element | Radius $r_i$/mm | Thickness $d_i$/mm | Distance $d_i$/mm | Glass Values |
|---|---|---|---|---|
| 41 | $r_1 = 96.466$ | $d_1 = 8.3$ | | BALF4 |
| | $r_2 = -76.076$ | $d_2 = 4.3$ | | SF54 |
| | $r_3 = -262.7$ | | | |
| | | | $d_3 = 140.5$ | |
| 52 | | $d_4 = 10.0$ | | BK7 |
| | $r_4 = 51.212$ | $d_5 = 3.0$ | | SK11 |
| 47 | $r_5 = -14.343$ | $d_6 = 2.0$ | | SFL6 |
| | $r_6 = -27.582$ | | | |
| 52 | | $d_7 = 70.0$ | BK7 | |
| | $r_7 = 403.88$ | $d_8 = 3.0$ | | SK2 |
| | $r_8 = -15.399$ | | | |
| 48 | $r_9 = -28.592$ | $d_9 = 2.0$ | | SFL6 |
| | $r_{10} = 43.401$ | $d_{10} = 3.0$ | | SSKN8 |
| | $r_{11} = -143.3$ | | | |
| 52 | | | $d_{11} = 70.0$ | BK7 |
| | $r_{12} = 31.623$ | $d_{12} = 4.0$ | | SK11 |
| 49 | $r_{13} = -14.962$ | $d_{13} = 2.0$ | | SF10 |
| | $r_{14} = -69.283$ | | | |
| 52 | | | $d_{14} = 10.0$ | BK7 |
| | $r_{15} = 151.79$ | $d_{15} = 4.0$ | | SSKN8 |
| 49 | $r_{16} = -11.363$ | $d_{16} = 2.0$ | | SFL6 |
| | $r_{17} = -19.953$ | | | |
| 52 | | | $d_{17} = 70.0$ | BK7 |
| | $r_{18} = 316.23$ | | | |
| | | $d_{18} = 4.0$ | | SSKNB |
| | $r_{19} = -16.079$ | | | |
| 50 | | $d_{19} = 2.0$ | | SFL6 |
| | $r_{20} = -34.974$ | | | |
| | $r_{21} = 29.427$ | | | |
| | | $d_{20} = 3.0$ | | SK5 |
| | $r_{22} = -199.53$ | | | |
| 52 | | | $d_{21} = 50.0$ | BK7 |
| | | | $d_1 = 2.0$ | AIR |
| | $r_{23} = -13.725$ | | | |
| 51 | | $d_{22} = 2.0$ | | SK11 |
| | $r_{24} = 51.955$ | | | |
| | | $d_{23} = 3.0$ | | SF10 |
| | $r_{25} = -104.41$ | | | |

TABLE II

| Optical Element | Radius $r_i$/mm | Thickness $d_i$/mm | Distance $d_i$/mm | Glass Values |
|---|---|---|---|---|
| 57.1,57.2 | $r_1 = 65.879$ | | | |
| | | $d_1 = 1.0$ | | SF10 |
| | $r_2 = 15.179$ | $d_2 = 1.5$ | | SSK50 |
| | $r_3 = -22.876$ | | | |
| 56 | $r_4 = 21.288$ | $d_3 = 3.0$ | | SSKN8 |
| | $r_5 = -9.8571$ | $d_4 = 1.0$ | | SFB |
| | $r_6 = -36.256$ | | | |
| | | | $d_5 = 37.2$ | BK7 |
| | $r_7 = 19.248$ | $d_6 = 5.0$ | | SK11 |
| | $r_8 = -5.7876$ | $d_7 = 2.0$ | | SFL6 |
| | $r_9 = -10.981$ | | | |
| | | | $d_8 = 56.83$ | SF1 |
| | $r_{10} = 77.736$ | $d_9 = 3.0$ | | SK2 |
| | $r_{11} = -10.218$ | | | |
| 48 | $r_{12} = -22.227$ | $d_{10} = 2.0$ | | SF10 |
| | $r_{13} = 28.799$ | $d_{11} = 3.0$ | | SF8 |
| | $r_{14} = -285.92$ | | | |
| 52 | | | $d_{12} = 42.99$ | SF1 |
| | $r_{15} = 330.18$ | $d_{13} = 4.0$ | | SSK51 |
| | $r_{16} = -11.383$ | $d_{14} = 2.0$ | | SF10 |
| | $r_{17} = -258.52$ | $d_{15} = 4.0$ | | SF1 |
| 49 | $r_{18} = 196.68$ | $d_{16} = 4.0$ | | SSKN8 |
| | $r_{19} = -7.1821$ | $d_{17} = 2.0$ | | SF55 |
| | $r_{20} = -10.0$ | | | |
| 52 | | | $d_{18} = 54.16$ | SF1 |
| | $r_{21} = 196.68$ | $d_{19} = 3.0$ | | SK2 |
| | $r_{22} = -9.7163$ | | | |
| 50 | $r_{23} = -24.76$ | $d_{20} = 2.0$ | | SF1 |
| | $r_{24} = 20.535$ | $d_{21} = 3.0$ | | F5 |
| | $r_{25} = -149.62$ | | | |

TABLE II-continued

| Optical Element | Radius $r_i$/mm | Thickness $d_i$/mm | Distance $d_i$/mm | Glass Values |
|---|---|---|---|---|
| 52 | | | $d_{22} = 38.29$ | SF1 |
| | | | $d_1 = 1.5$ | AIR |
| | $r_{26} = -18.701$ | $d_{23} = 1.0$ | | SSK51 |
| | $r_{27} = 4.5973$ | $d_{24} = 4.0$ | | SF1 |

TABLE II-continued

| Optical Element | Radius $r_i$/mm | Thickness $d_i$/mm | Distance $d_i$/mm | Glass Values |
|---|---|---|---|---|
| 51 | $r_{29} = 38.404$ | | | |
| | $r_{29} = -5.4639$ | $d_{25} = 2.0$ | | AIR |
| | $r_{30} = -31.623$ | $d_{26} = 1.0$ | | SF10 |

TABLE III

| Component System Number | | Radius $r_i$/mm | Thickness/Distance $d_i$/mm | Glass Values |
|---|---|---|---|---|
| Main Objective + In-Coupling Optic | 1 | 28.387 | 2.08 | |
| | 2 | −14.855 | 3.0 | BaF4 |
| | 3 | −35.277 | 1.0 | SF56A |
| | 4 | ∞ | 0 | |
| | 5 | ∞ | 48.62 | LAKN22 |
| | 6 | 20.833 | 0 | |
| Transmission Optic | 7 | −7.9433 | 4.0 | F5 |
| | 8 | −15.510 | 2.0 | SF56A |
| | 9 | ∞ | 0 | |
| | 10 | ∞ | 53.85 | LAKN22 |
| | 11 | 15.51 | 0 | |
| | 12 | 7.9433 | 2.0 | SF56A |
| | 13 | −7.9433 | 4.0 | F5 |
| | 14 | −15.51 | 2.0 | SF56A |
| | 15 | ∞ | 0 | |
| | 16 | ∞ | 53.85 | LAKN22 |
| | 17 | 15.51 | 0 | |
| | 18 | 7.9433 | 2.0 | SF56A |
| Endoscope Objective $\beta = 6$ Image Angle 45° | 19 | −7.9433 | 4.0 | F5 |
| | 20 | −15.51 | 2.0 | SF56A |
| | 21 | ∞ | 0 | |
| | 22 | ∞ | 53.85 | LANK22 |
| | 23 | 21.288 | 0 | |
| | 24 | −147.49 | 2.0 | SSKN8 |
| | 25 | 12.68 | 0 | |
| | 26 | −15.399 | 3.0 | SSKN8 |
| | 27 | −258.52 | 1.0 | SF56A |
| | 28 | ∞ | 0 | |
| | 29 | ∞ | 19.79 | SF10 |
| | 30 | −5.233 | 1.4 | |
| | 31 | −3.7584 | 2.0 | SF10 |
| | 32 | −76.076 | 1.0 | SK11 |
| | 33 | −4.5973 | 1.6 | |
| | 34 | −13.626 | 1.4 | BK7 |

Work distance d = 45.2 mm, Magnification $\beta = 6 \times$ Viewing field diameter 2L = 40 mm, image angle 45°

TABLE IV

| Component System Number | | Radius $r_i$/mm | Thickness/Distance $d_i$/mm | Glass Values |
|---|---|---|---|---|
| Main Objective + In-Coupling Optic | 1 | 28.387 | 2.08 | |
| | 2 | −14.855 | 3.0 | BaF4 |
| | 3 | −35.227 | 1.0 | SF56A |
| | 4 | ∞ | 0 | |
| | 5 | ∞ | 48.62 | LAKN22 |
| | 6 | 20.833 | 0 | |
| Transmission Optic | 7 | −7.9433 | 4.0 | F5 |
| | 8 | −15.510 | 2.0 | SF56A |
| | 9 | ∞ | ∞ | 0 |
| | 10 | ∞ | 53.85 | LAKN22 |
| | 11 | 15.51 | 0 | |
| | 12 | 7.9433 | 2.0 | SF56A |
| | 13 | −7.9433 | 4.0 | F5 |
| | 14 | −15.51 | 2.0 | SF56A |
| | 15 | ∞ | 0 | |
| | 16 | ∞ | 53.85 | LAKN22 |
| | 17 | 15.51 | 0 | |
| | 18 | 7.9433 | 2.0 | SF56A |
| | 19 | −7.9433 | 4.0 | F5 |

TABLE IV-continued

| Component System Number | Radius $r_i$/mm | Thickness/Distance $d_i$/mm | Glass Values |
|---|---|---|---|
| 20 | −15.51 | 2.0 | SF56A |
| 21 | ∞ | 0 | |
| 22 | ∞ | 53.85 | LAKN22 |
| 23 | 19.5208 | 0 | |
| 24 | −9.60378 | 3.0 | SSKN8 |
| 25 | −40.4719 | 1.0 | SF56A |
| 26 | 11.1552 | 0 | |
| 27 | −250.0 | 2.0 | F5 |
| 28 | ∞ | 0 | |
| 29 | ∞ | 17.11 | SF10 |
| 30 | −6.1514 | 0.5 | |
| 31 | −3.25855 | 2.0 | SF10 |
| 32 | 69.5948 | 1.0 | SK11 |
| 33 | −3.37032 | 1.0 | |
| 34 | −11.0651 | 1.0 | BaF4 |
| 35 | −3.79897 | 1.0 | |
| 36 | −8.59761 | 1.5 | BK7 |

Work distance d = 46.0 mm, Magnification β = 8 × Viewing field diameter 2L = 52 mm, Image angle 60°

What is claimed is:

1. A stereoendoscope for viewing an object along a pair of stereo beam paths, comprising:

a stereoscopic viewing apparatus including optical means for defining a pair of stereo beam paths with each beam path defining an apparatus pupil having an apparatus pupil diameter; and said stereo beam paths being separated by a distance defining a stereo basis;

an endoscope attachment;

said endoscope attachment and said stereoscopic viewing apparatus conjointly defining in-coupling means for coupling said pair of stereo beam paths into said endoscope attachment;

said endoscope attachment including:

an optical lens system for receiving and guiding both of said stereo beam paths in common therein;

said optical lens system defining a pupil of said endoscope attachment;

said optical lens system further including imaging optical means for generating an intermediate image of the object and for generating an intermediate image of said pupil of said endoscope attachment;

said imaging optical means having a clear diameter;

said in-coupling means including: a main objective for imaging said intermediate image of said object at infinity; and, additional optical imaging means;

said additional optical imaging means and said main objective conjointly imaging said apparatus pupils demagnified into said intermediate image of said pupil of said endoscope attachment so as to cause the image of the sum of the stereo basis and of the pupil diameter to be less than or equal to said clear diameter of said imaging optical means; and, said intermediate image being generated at a stereo angle (α') and stereo component images being generated in said stereoscopic viewing apparatus while maintaining said stereo angle (α').

2. The stereoendoscope of claim 1, said intermediate image being a first intermediate image and said imaging optical means comprising an endoscope objective for generating a second intermediate image and a transmission system; and, said transmission system being adapted to image said second intermediate image into said first intermediate image.

3. The stereoendoscope of claim 2, said in-coupling means including a part of said imaging optical means and said part and said main objective conjointly defining an inverted telescope; and, said first intermediate image lying between said main objective and said in-coupling means.

4. The stereoendoscope of claim 3, said in-coupling means comprising an objective and a field lens.

5. The stereoendoscope of claim 1, further comprising a component objective, a prism system and a CCD-receiver means all arranged downstream of said main objective.

6. A stereoendoscope for viewing an object along a pair of stereo beam paths, comprising:

a sterioscopic viewing apparatus including optical means for defining a pair of stereo beam paths with each beam path defining an apparatus pupil having an apparatus pupil diameter; and said stereo beam paths being separated by a distance defining a stereo basis;

an endoscope attachment;

said endoscope attachment and said stereoscopic viewing apparatus conjointly defining in-coupling means for coupling said pair of stereo beam paths into said endoscope attachment;

said endoscope attachment including:

an optical lens system for receiving and guiding both of said stereo beam paths in common therein;

said optical lens system defining a pupil of said endoscope attachment;

said optical lens system further including imaging optical means for generating an intermediate image of the object and for generating an intermediate image of said pupil of said endoscope attachment;

said imaging optical means having a clear diameter;

said in-coupling means including: a main objective for imaging said intermediate image of said object at infinity; and, additional optical imaging means; and, said additional optical imaging means and said main objective conjointly imaging said apparatus pupils demagnified into said intermediate image of said pupil of said endoscope attachment so as to cause the image of the sum of the stereo basis and of the pupil diameter to be less than or equal to said clear diameter of said imaging optical means;

the following condition:

$$0.5 < \frac{(2L')}{D} < 1$$

being satisfied for imaging the object; and, the following condition:

$$0.5 < \frac{2(2A + p)}{D} < 1$$

being satisfied for imaging said apparatus pupils; and, at the same time, the condition:

$$\frac{p}{p'} = \frac{A}{A'} = \frac{f_2}{f_3}.$$

being satisfied for in-coupling into said main objective; and, wherein:

2L' is the field diameter of said intermediate image;

$f_2$ is the focal length of said in-coupling means;

$f_3$ is the focal length of said main objective;

D is the clear diameter of said optical lens system;

2A' is the diameter of the apparatus pupils;

2A is the diameter of the image of the apparatus pupils within the endoscope attachment;

2p+2A is the image of the stereo basis within the endoscope attachment; and,

2p'+2A' is the stereo basis of the stereoscopic viewing apparatus.

7. The stereoendoscope of claim 6, said endoscope attachment being a rod-shaped attachment and said main objective being part of said rod-shaped attachment; and, said main objective being disposed forward of said transmission system in the viewing direction.

8. The stereoendoscope of claim 7, wherein a plurality of mutually intertwining beam paths are guided through said attachment.

9. The stereoendoscope of claim 8, said optical lens system including an object-end objective; a rearward imaging system, a rearward field lens system and a forward imaging system.

10. The stereoendoscope of claim 9, said optical lens system defining an optical axis; and, wherein said intermediate images extend over approximately all of said clear diameter (D).

11. The stereoendoscope of claim 10, further comprising:

light refracting optical elements for expanding said stereo basis all disposed downstream of said transmission system and said in-coupling means.

12. The stereoendoscope of claim 11, said endoscope attachment including glass rods for extending the structural length thereof.

13. The stereoendoscope of claim 12, said transmission system comprising a gradient lens having a radial refractive index.

14. The stereoendoscope of claim 13, said transmission system being assembled from identical and symmetrical cemented optical elements.

15. The stereoendoscope of claim 14, said transmission system further including a cylinder disposed between said cemented optical elements; and, said cylinder being made of optically transparent material.

16. The stereoendoscope of claim 14, wherein said optical elements are made of glasses resistant to heat and environmental influences.

17. The stereoendoscope of claim 14, wherein the types of glass used for said cemented optical elements have a thermal coefficient of expansion which is approximately all the same.

18. The stereoendoscope of claim 15, said cemented optical elements each comprising two meniscus lenses and a biconvex lens disposed between said meniscus lenses.

19. The stereoendoscope of claim 15, said cemented optical elements each comprising two meniscus lenses and a spherical lens disposed between said meniscus lenses.

20. The stereoendoscope of claim 18, each of said meniscus lenses having an axial length less than one-half of the diameter thereof.

21. The stereoendoscope of claim 18, wherein the distance between said meniscus lenses and said cylinder is zero.

22. An endoscope attachment for a stereoscopic viewing apparatus for viewing an object, the stereoscopic viewing apparatus defining a pair of stereo beam paths with each beam path defining an apparatus pupil having an apparatus pupil diameter, said stereo beam paths being separated by a distance defining a stereo basis and the stereoscopic viewing apparatus including a main objective, said endoscope attachment comprising:

an optical lens system for receiving and guiding both of said stereo beam paths in common therein;

said optical lens system defining a pupil of said endoscope attachment;

said optical lens system further including imaging optical means for generating an intermediate image of the object and for generating an intermediate image of said pupil of said attachment;

said imaging optical means having a clear diameter;

an additional optical imaging means;

said additional optical imaging means and said main objective of said stereoscopic viewing apparatus conjointly defining in-coupling means for coupling said pair of stereo beam paths into said endoscope attachment; said main objective imaging said intermediate image at infinity and said additional optical imaging means and said main objective conjointly imaging said apparatus pupils demagnified into said intermediate image of said pupil of said endoscope attachment so as to cause the image of the sum of the stereo basis and of the pupil diameter to be less than or equal to said clear diameter of said imaging optical means; and, said intermediate image being generated at a stereo angle ($\alpha'$) and stereo component images being generated in said stereoscopic viewing apparatus while maintaining said stereo angle ($\alpha'$).

23. The endoscope attachment of claim 22, said intermediate image being a first intermediate image and said imaging optical means comprising an endoscope objective for generating a second intermediate image and a transmission system; and, said transmission system being adapted to image said second intermediate image into said first intermediate image.

24. The endoscope attachment of claim 23, said in-coupling means including a part of said imaging optical means and said part and said main objective conjointly defining an inverted telescope; and, said first intermediate image lying between said main objective and said in-coupling means.

25. The endoscope attachment of claim 24, said in-coupling means comprising an objective and a field lens.

26. An endoscope attachment for a stereoscopic viewing apparatus for viewing an object, the stereoscopic viewing apparatus defining a pair of stereo beam paths with each beam path defining an apparatus pupil having an apparatus pupil diameter, said stereo beam paths being separated by a distance defining a stereo basis and the stereoscopic viewing apparatus including a main objective, said endoscope attachment comprising:

an optical lens system for receiving and guiding both of said stereo beam paths in common therein;

said optical lens system defining a pupil of said endoscope attachment;

said optical lens system further including imaging optical means for generating an intermediate image of the object and for generating an intermediate image of said pupil of said attachment;

said imaging optical means having a clear diameter;

an additional optical imaging means; and, said additional optical imaging means and said main objective of said stereoscopic viewing apparatus conjointly defining in-coupling means for coupling said pair of stereo beam paths into said endoscope attachment; said main objective imaging said intermediate image at infinity and said additional optical imaging means and said main objective conjointly imaging said apparatus pupils demagnified into said intermediate image of said pupil of said endoscope attachment so as to cause the image of the sum of the stereo basis and of the pupil diameter to be less than or equal to said clear diameter of said imaging optical means;

the following condition:

$$0.5 < \frac{(2L')}{D} < 1$$

being satisfied for imaging the object; and, the following condition:

$$0.5 < \frac{2(2A+p)}{D} < 1$$

being satisfied for imaging said apparatus pupils; and, at the same time, the condition:

$$\frac{p}{p'} = \frac{A}{A'} = \frac{f_2}{f_3}.$$

being satisfied for in-coupling into said main objective; and, wherein:

2L' is the field diameter of said intermediate image;

$f_2$ is the focal length of said in-coupling means;

$f_3$ is the focal length of said main objective;

D is the clear diameter of said optical lens system;

2A' is the diameter of the apparatus pupils;

2A is the diameter of image of the apparatus pupils within the endoscope attachment;

2p+2A is the image of the stereo basis within the endoscope attachment; and,

2p'+2A' is the stereo basis of the stereoscopic viewing apparatus.

27. An endoscope attachment for a stereoscopic viewing apparatus for viewing an object, the stereoscopic viewing apparatus defining a pair of stereo beam paths having respective apparatus pupils of an apparatus pupil diameter and the stereo beam paths being separated by a distance defining a stereo basis, said endoscope attachment comprising:

an optical lens system for receiving and guiding both of said stereo beam paths in common therein;

said optical lens system further defining a pupil of said endoscope attachment;

said optical lens system further including imaging optical means for generating an intermediate image of the object and for generating an intermediate image of said pupil of said endoscope attachment;

said imaging optical means having a clear diameter;

in-coupling means for coupling said pair of stereo beam paths into said endoscope attachment;

said in-coupling means including a main objective and additional optical imaging means;

said main objective imaging said intermediate image at infinity and said main objective and said additional optical imaging means conjointly imaging said apparatus pupils of said stereoscopic viewing apparatus demagnified into said intermediate image of said pupil of said endoscope attachment so as to cause the image of the sum of the stereo basis and of the pupil diameter to be less than or equal to said clear diameter of said optical lens system; and, said intermediate image being generated at a stereo angle ($\alpha'$) and stereo component images being generated in said stereoscopic viewing apparatus while maintaining said stereo angle ($\alpha'$).

28. The endoscope attachment of claim 27, said intermediate image being a first intermediate image and said imaging optical means comprising an endoscope objective for generating a second intermediate image and a transmission system; and, said transmission system being adapted to image said second intermediate image into said first intermediate image.

29. The endoscope attachment of claim 28, said in-coupling means including a part of said imaging optical means and said part and said main objective conjointly defining an inverted telescope; and, said first intermediate image lying between said main objective and said in-coupling means.

30. The endoscope attachment of claim 29, said in-coupling means comprising an objective and a field lens.

31. An endoscope attachment for a stereoscopic viewing apparatus for viewing an object, the stereoscopic viewing apparatus defining a pair of stereo beam paths having respective apparatus pupils of an apparatus pupil diameter and the stereo beam paths being separated by a distance defining a stereo basis, said endoscope attachment comprising:

an optical lens system for receiving and guiding both of said stereo beam paths in common therein;

said optical lens system defining a pupil of said endoscope attachment;

said optical lens system further including imaging optical means for generating an intermediate image of the object and for generating an intermediate image of said pupil of said endoscope attachment;

said imaging optical means having a clear diameter;

in-coupling means for coupling said pair of stereo beam paths into said endoscope attachment;

said in-coupling means including a main objective and additional optical imaging means; and, said main objective imaging said intermediate image at infinity and said main objective and said additional optical imaging means conjointly imaging said apparatus pupils of said stereoscopic viewing apparatus demagnified into said intermediate image of said pupil of said endoscope attachment so as to cause the image of the sum of the stereo basis and of the pupil diameter to be less than or equal to said clear diameter of said optical lens system;

the following condition:

$$0.5 < \frac{(2L')}{D} < 1$$

being satisfied for imaging the object; and, the following condition:

$$0.5 < \frac{2(2A+p)}{D} < 1$$

being satisfied for imaging said apparatus pupils; and, at the same time, the condition:

$$\frac{p}{p'} = \frac{A}{A'} = \frac{f_2}{f_3}.$$

being satisfied for in-coupling into said main objective; and, wherein:

L' is the field diameter of said intermediate image;

$f_2$ is the focal length of said in-coupling means;

$f_3$ is the focal length of said main objective;

D is the clear diameter of said optical lens system;

A' is the diameter of the apparatus pupils;

2A is the diameter of image of the apparatus pupils within the endoscope attachment;

2p+2A is the image of the stereo basis within the endoscope attachment; and,

2p'+2A' is the stereo basis of the stereoscopic viewing apparatus.

\* \* \* \* \*

UNITED STATES PATENT AND TRADEMARK OFFICE
CERTIFICATE OF CORRECTION

PATENT NO. : 5,612,816

DATED : March 18, 1997

INVENTOR(S) : Fritz Strähle, Ulrich Sander and Uwe Vry

It is certified that error appears in the above-identified patent and that said Letters Patent is hereby corrected as shown below:

In column 1, line 3, after the title: insert -- RELATED APPLICATIONS --.

In column 2, line 6: delete "tile" and substitute -- the -- therefor.

In column 3, line 58: delete "elements and" and substitute -- elements, and -- therefor.

In column 5, line 10: after "system 49 and", please insert -- the second intermediate image 55 is formed--.

In column 5, line 26: delete "(47 to 51" and substitute -- (47 to 51) -- therefor.

In column 5, line 51: delete "FIG. 1b and 1c" and insert -- FIGS. 1b and 1c -- therefor.

In column 5, line 52: delete "FIG. 2b and 2c" and insert -- FIGS. 2b and 2c -- therefor.

UNITED STATES PATENT AND TRADEMARK OFFICE
CERTIFICATE OF CORRECTION

PATENT NO. : 5,612,816

DATED : March 18, 1997

INVENTOR(S) : Fritz Strähle, Ulrich Sander and Uwe Vry

It is certified that error appears in the above-identified patent and that said Letters Patent is hereby corrected as shown below:

In column 5, line 55: delete "(FIGS. 1b and 1c" and insert -- (FIGS. 1b and 1c) -- therefor.

In column 5, line 61: delete "FIGS. 1b and 1c" and insert -- FIGS. 1b and 1c and -- therefor.

In column 6, line 47: delete "tile" and substitute -- the -- therefor.

In column 8, please delete Table I and substitute Table I on page 4 of 9 of this certificate of correction.

In columns 8, 9 and 10, please delete Table II and substitute Table II on page 5 of 9 of this certificate of correction.

In column 10, please delete Table III and substitute Table III on pages 6 and 7 of 9 of this certificate of correction.

In columns 10 and 11, please delete Table IV and substitute Table IV on pages 8 and 9 of 9 of this certificate of correction.

UNITED STATES PATENT AND TRADEMARK OFFICE
CERTIFICATE OF CORRECTION

PATENT NO. : 5,612,816

DATED : March 18, 1997

INVENTOR(S) : Fritz Strähle, Ulrich Sander and Uwe Vry

It is certified that error appears in the above-identified patent and that said Letters Patent is hereby corrected as shown below:

In column 12, line 36: delete "sterioscopic" and substitute -- stereoscopic -- therefor.

In column 18, line 4: delete "L'" and substitute -- 2L' -- therefor.

In column 18, line 10: delete "A'" and substitute -- 2A' -- therefor.

Signed and Sealed this

Twenty-fourth Day of June, 1997

*Attest:*

BRUCE LEHMAN

*Attesting Officer*   *Commissioner of Patents and Trademarks*

Table I

| Optical Element | Radius $r_i$/mm | Thickness $d_i$/mm | Distance $d_i$/mm | Glass Values |
|---|---|---|---|---|
| 41 | $r_1 = 96.466$ | $d_1 = 8.3$ | | BALF4 |
| | $r_2 = -76.076$ | $d_2 = 4.3$ | | SF54 |
| | $r_3 = -262.7$ | | | |
| 52 | | | $d_3 = 140.5$ | |
| | | | $d_4 = 10.0$ | BK7 |
| | $r_4 = 51.212$ | $d_5 = 3.0$ | | SK11 |
| 47 | $r_5 = -14.343$ | $d_6 = 2.0$ | | SFL6 |
| | $r_6 = -27.582$ | | | |
| 52 | | | $d_7 = 70.0$ | BK7 |
| | $r_7 = 403.88$ | $d_8 = 3.0$ | | SK2 |
| | $r_8 = -15.399$ | | | |
| 48 | $r_9 = -28.592$ | $d_9 = 2.0$ | | SFL6 |
| | $r_{10} = 43.401$ | $d_{10} = 3.0$ | | SSKN8 |
| | $r_{11} = -143.3$ | | | |
| 52 | | | $d_{11} = 70.0$ | BK7 |
| | $r_{12} = 31.623$ | $d_{12} = 4.0$ | | SK11 |
| 49 | $r_{13} = -14.962$ | $d_{13} = 2.0$ | | SF10 |
| | $r_{14} = -69.283$ | | | |
| 52 | | | $d_{14} = 10.0$ | BK7 |
| | $r_{15} = 151.79$ | $d_{15} = 4.0$ | | SK11 |
| 49 | $r_{16} = -11.363$ | $d_{16} = 2.0$ | | SFL6 |
| | $r_{17} = -19.953$ | | | |
| 52 | | | $d_{17} = 70.0$ | BK7 |
| | $r_{18} = 316.23$ | | | |
| | | $d_{18} = 4.0$ | | SSKN8 |
| | $r_{19} = -16.079$ | | | |
| 50 | | $d_{19} = 2.0$ | | SFL6 |
| | $r_{20} = -34.974$ | | | |
| | $r_{21} = 29.427$ | | | |
| | | $d_{20} = 3.0$ | | SK5 |
| | $r_{22} = -199.53$ | | | |
| 52 | | | $d_{21} = 50.0$ | BK7 |
| | | | $d_1 = 2.0$ | AIR |
| | $r_{23} = -13.725$ | | | |
| 51 | | $d_{22} = 2.0$ | | SK11 |
| | $r_{24} = 51.955$ | | | |
| | | $d_{23} = 3.0$ | | SF10 |
| | $r_{25} = -104.41$ | | | |

Table II

| Optical Element | Radius $r_i$/mm | Thickness $d_i$/mm | Distance $d_i$/mm | Glass Values |
|---|---|---|---|---|
| 57.1, 57.2 | $r_1 = 65.879$ | $d_1 = 1.0$ | | SF10 |
| | $r_2 = 15.179$ | $d_2 = 1.5$ | | SSK50 |
| | $r_3 = -22.876$ | | | |
| 56 | $r_4 = 21.288$ | $d_3 = 3.0$ | | SSKN8 |
| | $r_5 = -9.8571$ | $d_4 = 1.0$ | | SF8 |
| | $r_6 = -36.256$ | | | |
| 52 | | | $d_5 = 37.2$ | BK7 |
| | $r_7 = 19.248$ | $d_6 = 5.0$ | | SK11 |
| 47 | $r_8 = -5.7876$ | $d_7 = 2.0$ | | SFL6 |
| | $r_9 = -10.981$ | | | |
| 52 | | | $d_8 = 56.83$ | SF1 |
| | $r_{10} = 77.736$ | $d_9 = 3.0$ | | SK2 |
| | $r_{11} = -10.218$ | | | |
| 48 | $r_{12} = -22.227$ | $d_{10} = 2.0$ | | SF10 |
| | $r_{13} = 28.799$ | $d_{11} = 3.0$ | | SF8 |
| | $r_{14} = -285.92$ | | | |
| 52 | | | $d_{12} = 42.99$ | SF1 |
| | $r_{15} = 330.18$ | $d_{13} = 4.0$ | | SSK51 |
| | $r_{16} = -11.383$ | $d_{14} = 2.0$ | | SF10 |
| | $r_{17} = -258.52$ | $d_{15} = 4.0$ | | SF1 |
| 49 | $r_{18} = 196.68$ | $d_{16} = 4.0$ | | SSKN8 |
| | $r_{19} = -7.1821$ | $d_{17} = 2.0$ | | SF55 |
| | $r_{20} = -10.0$ | | | |
| 52 | | | $d_{18} = 54.16$ | SF1 |
| | $r_{21} = 196.68$ | $d_{19} = 3.0$ | | SK2 |
| | $r_{22} = -9.7163$ | | | |
| 50 | $r_{23} = -24.76$ | $d_{20} = 2.0$ | | SF1 |
| | $r_{24} = 20.535$ | $d_{21} = 3.0$ | | F5 |
| | $r_{25} = -149.62$ | | | |
| 52 | | | $d_{22} = 38.29$ | SF1 |
| | | $d_1 = 1.5$ | | AIR |
| | $r_{26} = -18.701$ | $d_{23} = 1.0$ | | SSK51 |
| | $r_{27} = 4.5973$ | $d_{24} = 4.0$ | | SF1 |
| 51 | $r_{28} = 38.404$ | | | AIR |
| | $r_{29} = -5.4639$ | $d_{25} = 2.0$ | | SF10 |
| | $r_{30} = -31.623$ | $d_{26} = 1.0$ | | |

Table III

| Component System Number | | Radius $r_i$/mm | Thickness/Distance $d_i$/mm | Glass Values |
|---|---|---|---|---|
| | | | 2.08 | |
| Main Objective + In-Coupling Optic | 1 | 28.387 | 3.0 | BaF4 |
| | 2 | -14.855 | 1.0 | SF56A |
| | 3 | -35.227 | 0 | |
| | 4 | ∞ | 48.62 | LAKN22 |
| | 5 | ∞ | 0 | |
| | 6 | 20.833 | 4.0 | F5 |
| Transmission Optic | 7 | -7.9433 | 2.0 | SF56A |
| | 8 | -15.510 | 0 | |
| | 9 | ∞ | 53.85 | LAKN22 |
| | 10 | ∞ | 0 | |
| | 11 | 15.51 | 2.0 | SF56A |
| | 12 | 7.9433 | 4.0 | F5 |
| | 13 | -7.9433 | 2.0 | SF56A |
| | 14 | -15.51 | 0 | |
| | 15 | ∞ | 53.85 | LAKN22 |
| | 16 | ∞ | 0 | |
| | 17 | 15.51 | 2.0 | SF56A |
| | 18 | 7.9433 | 4.0 | F5 |
| | 19 | -7.9433 | 2.0 | SF56A |
| | 20 | -15.51 | 0 | |
| | 21 | ∞ | 53.85 | LAKN22 |
| | 22 | ∞ | 0 | |
| | 23 | 21.288 | 2.0 | SSKN8 |
| | 24 | -147.49 | 0 | |

Endoscope Objective
β = 6
Image Angle 45°

| | | | |
|---|---|---|---|
| 25 | 12.68 | 3.0 | SSKN8 |
| 26 | -15.399 | 1.0 | SF56A |
| 27 | -258.52 | 0 | |
| 28 | ∞ | 19.79 | SF10 |
| 29 | ∞ | 1.4 | |
| 30 | -5.233 | 2.0 | SF10 |
| 31 | -3.7584 | 1.0 | SK11 |
| 32 | -76.076 | 1.6 | |
| 33 | -4.5973 | 1.4 | BK7 |
| 34 | -13.626 | | |

Work distance d = 45.2 mm, Magnification β = 6x
Viewing field diameter 2L = 40 mm, Image angle 45°

Table IV

| Component System Number | | Radius $r_i$/mm | Thickness/Distance $d_i$/mm | Glass Values |
|---|---|---|---|---|
| Main Objective + In-Coupling Optic | 1 | 28.387 | 2.08 | BaF4 |
| | 2 | −14.855 | 3.0 | SF56A |
| | 3 | −35.227 | 1.0 | |
| | 4 | ∞ | 0 | LAKN22 |
| | 5 | ∞ | 48.62 | |
| | 6 | 20.833 | 0 | F5 |
| Transmission Optic | 7 | −7.9433 | 4.0 | SF56A |
| | 8 | −15.510 | 2.0 | |
| | 9 | ∞ | 0 | LAKN22 |
| | 10 | ∞ | 53.85 | |
| | 11 | 15.51 | 0 | SF56A |
| | 12 | 7.9433 | 2.0 | F5 |
| | 13 | −7.9433 | 4.0 | SF56A |
| | 14 | −15.51 | 2.0 | |
| | 15 | ∞ | 0 | LAKN22 |
| | 16 | ∞ | 53.85 | |
| | 17 | 15.51 | 0 | SF56A |
| | 18 | 7.9433 | 2.0 | F5 |
| | 19 | −7.9433 | 4.0 | SF56A |
| | 20 | −15.51 | 2.0 | |
| | 21 | ∞ | 0 | LAKN22 |
| | 22 | ∞ | 53.85 | |
| | 23 | 19.5208 | 0 | SSKN8 |
| | 24 | −9.60378 | 3.0 | |

| | | | |
|---|---|---|---|
| | | 1.0 | SF56A |
| 25 | −40.4719 | | |
| | | 0 | |
| 26 | 11.1552 | | |
| | | 2.0 | F5 |
| 27 | −250.0 | | |
| | | 0 | |
| 28 | ∞ | | |
| | | 17.11 | SF10 |
| 29 | ∞ | | |
| | | 0.5 | |
| 30 | −6.1514 | | |
| | | 2.0 | SF10 |
| 31 | −3.25855 | | |
| | | 1.0 | SK11 |
| 32 | 69.5948 | | |
| | | 1.0 | |
| 33 | −3.37032 | | |
| | | 1.0 | BaF4 |
| 34 | −11.0651 | | |
| | | 1.0 | |
| 35 | −3.79897 | | |
| | | 1.5 | BK7 |
| 36 | −8.59761 | | |

Work distance d = 46.0 mm, Magnification β = 8x
Viewing field diameter 2L = 52 mm, Image angle 60°